(12) United States Patent
Amley et al.

(10) Patent No.: US 7,637,279 B2
(45) Date of Patent: Dec. 29, 2009

(54) SHUTTLE VALVE (75) Inventors: Joseph M. Amley, Suwanee, GA (US);
Danny F. Lincoln, Commerce, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 306 days.

(21) Appl. No.: 11/275,646

(22) Filed: Jan. 20, 2006

(65) Prior Publication Data
US 2007/0221275 A1    Sep. 27, 2007

(51) Int. Cl.
*G05D 11/00* (2006.01)
*F16K 21/04* (2006.01)

(52) U.S. Cl. .................. 137/102; 137/512
(58) Field of Classification Search ............. 137/102, 137/112, 512, 113
See application file for complete search history.

(56) References Cited

U.S. PATENT DOCUMENTS

| | | | |
|---|---|---|---|
| 2,311,851 A | | 2/1943 | McClure |
| 2,486,046 A | * | 10/1949 | Majneri ............... 137/637.1 |
| 3,073,332 A | | 1/1963 | Strader |
| 3,827,601 A | * | 8/1974 | Magrath et al. ............... 222/83 |
| 4,084,606 A | | 4/1978 | Mittleman |
| 4,271,989 A | | 6/1981 | O'Neill et al. |
| 4,596,558 A | | 6/1986 | Smith et al. |
| 4,666,429 A | | 5/1987 | Stone |
| 4,798,589 A | | 1/1989 | Tseo |
| 4,819,684 A | | 4/1989 | Zaugg et al. |
| 4,844,700 A | | 7/1989 | Henderson |
| 5,147,333 A | | 9/1992 | Raines |

(Continued)

FOREIGN PATENT DOCUMENTS

DE         9114493 U1     2/1992

(Continued)

OTHER PUBLICATIONS

International Search Report for PCT/US2006/045559, mailed on Mar. 19, 2007 (5 pages).

(Continued)

*Primary Examiner*—John Rivell
*Assistant Examiner*—Atif H Chaudry
(74) *Attorney, Agent, or Firm*—Wood, Herron & Evans, LLP (57) ABSTRACT

A shuttle valve (12,150,230) is provided having a body (44, 152,232) defining an interior chamber (46,154,234). The valve (12,150,230) includes inlet (16,158,238), outlet (18, 160,240) and common (14,156,236) ports that are coupled to the body (44,152,232). A shuttle (48, 162,242) is translatably disposed within the chamber (46,154,234) between a first position wherein the inlet (16,158,238) and common (14,156, 236) ports are fluidicly coupled and the common (14,156, 236) and outlet (18,160,240) ports are fluidicly uncoupled, and a second position wherein the outlet (18,160,240) and common (14,156,236) ports are fluidicly coupled and the common (14,156,236) and inlet (16,158,238) ports are fluidicly uncoupled. A first check valve (50,50,50) coupled to the inlet port (16,158,238) to permit fluid flow through the inlet port (16,158,238) into the chamber (46,154,234) and to prevent fluid from discharging therethrough. A second check valve (50,50,50) is coupled to the outlet port (18,160,240) in a manner to permit fluid to discharge from the chamber (46, 154,234) through the outlet port (18,160,240) and to prevent fluid from flowing through the outlet port (18,160,240) into the chamber (46,154,234).

40 Claims, 5 Drawing Sheets

U.S. PATENT DOCUMENTS

| | | |
|---|---|---|
| 5,176,658 A | 1/1993 | Ranford |
| 5,439,022 A * | 8/1995 | Summers et al. ............ 137/102 |
| 5,573,515 A | 11/1996 | Wilson et al. |
| 5,800,397 A | 9/1998 | Wilson et al. |
| 5,813,401 A * | 9/1998 | Radcliff et al. ......... 128/205.24 |
| 5,882,343 A | 3/1999 | Wilson et al. |
| 6,059,747 A | 5/2000 | Bruggeman et al. |
| 6,099,511 A | 8/2000 | Devos et al. |
| 6,221,045 B1 | 4/2001 | Duchon et al. |
| 6,344,030 B1 | 2/2002 | Duchon et al. |
| 6,626,862 B1 | 9/2003 | Duchon et al. |
| 6,656,157 B1 | 12/2003 | Wilson et al. |
| 6,662,819 B1 * | 12/2003 | Watson ....................... 137/113 |
| 6,866,654 B2 | 3/2005 | Callan et al. |
| 7,225,830 B1 * | 6/2007 | Kershaw .................. 137/512.1 |
| 2002/0183616 A1 | 12/2002 | Toews et al. |
| 2004/0143212 A1 | 7/2004 | Trombley, III et al. |
| 2005/0096627 A1 | 5/2005 | Howard |

FOREIGN PATENT DOCUMENTS

| | | |
|---|---|---|
| EP | 0202384 A1 | 11/1986 |
| EP | 1473054 A1 | 11/2004 |
| WO | 9318806 A1 | 9/1993 |
| WO | 9320864 A1 | 10/1993 |
| WO | 0000241 A2 | 1/2000 |
| WO | 0136026 A1 | 5/2001 |
| WO | 0158506 A2 | 8/2001 |

OTHER PUBLICATIONS

Written Opinion for PCT/US2006/045559, mailed on Mar. 19, 2007 (7 pages).

International Preliminary Report on Patentability for counterpart application No. PCT/US2006/045559 mailed on May 20, 2008 (22 pages).

* cited by examiner

SHUTTLE VALVE

FIELD OF THE INVENTION

The present invention is directed to a valve and, more particularly, to a shuttle valve that can advantageously be utilized in a system for dispensing medical fluids intravenously to a patent.

BACKGROUND

Various systems are known in the medical arts for dispensing a variety of fluids, such as saline and medication intravenously to a patient. One known system includes a three way stopcock valve and a syringe that are manually operated by a caregiver. An inlet port of the valve is fluidically coupled to a source of fluid, while a common port is fluidically coupled to a syringe and an outlet port is fluidically coupled to a patient. While systems of this general type have been successfully utilized, they are subject to some disadvantages. In the first instance, when a caregiver enters a patient's room to administer an intravenous fluid, the caregiver must first check the stopcock valve to ensure the valve position is selected to fluidically couple the inlet and common ports, thereby fluidically coupling the source of fluid and the syringe. Next the caregiver must go to the syringe and draw fluid into the syringe. The caregiver must then go back to the stopcock valve and select the valve position that fluidically couples the common and outlet ports, thereby fluidically coupling the syringe and the patient. Then back to the syringe to administer the fluid. If the valve and the syringe are not in close proximity to one another, this process is inconvenient and time consuming for the caregiver.

There is also the risk of error by the caregiver, as well as the potential for inadvertent fluidic coupling of the source of fluid to the valve port coupled to the patient such as upon failure of the valve due to misuse.

SUMMARY

In response to the foregoing problems associated with valves requiring active selection by a caregiver of the desired port coupling, the present invention provide a shuttle valve that passively and reliably selects the ports to be fluidicly coupled. This is advantageously accomplished according to the principles of the present invention by coupling a first check valve to an inlet port of the shuttle valve in a manner to permit fluid flow through the inlet port into a chamber defined by a body of the shuttle valve and to prevent fluid from discharging from the chamber through the inlet port, and by coupling a second check valve to the outlet port in a manner to permit fluid to discharge from the chamber through the outlet port and to prevent fluid from flowing through the outlet port into the chamber. Also in accordance with the principles of the present invention, at least a portion of the chamber may be vented to atmosphere. Accordingly, a pressure differential can be created across a shuttle that is translatably disposed within the interior chamber, so that the shuttle is responsive to varying a fluid pressure at a common port of the shuttle valve, which can be fluidically coupled to a syringe, to move the shuttle between first and second positions within the chamber in response to the action of filling and emptying the syringe.

More particularly, the shuttle is moveable into a first position in response to decreased fluid pressure at the common port, caused by retracting the plunger of the syringe fluidicly coupled to the common port. When the shuttle is in the first position, the inlet port and the common port are fluidicly coupled so as to allow the syringe to be filled. The shuttle is moveable into the second position in response to increased fluid pressure at the common port caused by advancing or pushing the plunger of the syringe. In the second position, the outlet port and the common port are fluidicly coupled so as to expel the fluid in the syringe to the patient. As a result, the caregiver can easily fill and empty the syringe without having to manually operate the valve, thereby overcoming the drawbacks of the stopcock arrangement.

The inlet port and outlet port are fluidicly uncoupled, regardless of the position of the shuttle within the interior chamber. Accordingly, undesired direct coupling of the source of fluid coupled to the inlet port and a patient coupled to the outlet port, is also avoided. This is advantageously accomplished in accordance with the principles of the present invention by providing a plurality of seals disposed about a periphery of the shuttle and in slidable, sealing engagement with an inner surface of the body of the shuttle valve.

The common port can be fluidicly coupled with either the inlet or outlet port via various flow passages which can include passages formed within the body of the shuttle, such as longitudinally extending and radially extending passages, as well as apertures formed in the body of the shuttle valve.

Shuttle valves have been used in various technologies including the medical arts where shuttle valves have been used as part of a system to inject a patient with radiographic material. However, with known shuttle valves, the shuttle is normally biased into a first position, and either a hydraulic fluid, or the fluid to be expelled, drives the shuttle to a second position during expulsion of the fluid. But a spring or secondary driving fluid is necessary to bias the shuttle back to the first position when hydraulic or communicating fluid pressure ceases. Valves of this type do not change positions solely in response to the pressure (positive or negative) of the fluid intended to be communicated through the valve. The incorporation of one or more springs in valves of this type add complexity and cost to the valve. Furthermore, if the spring is made of a ferrous metal, the valves are not suitable for use within a Magnetic Resonance Imaging (MRI) device thereby limiting the utility of the valve in certain medical situations.

By virtue of the foregoing, there is provided a shuttle valve that passively and reliably selects the ports to be coupled.

BRIEF DESCRIPTION OF THE DRAWINGS

These and other features, aspects, and advantages of the present invention will become better understood with regard to the following description, appended claims and accompanying drawings wherein:

DETAILED DESCRIPTION

Figure 1:
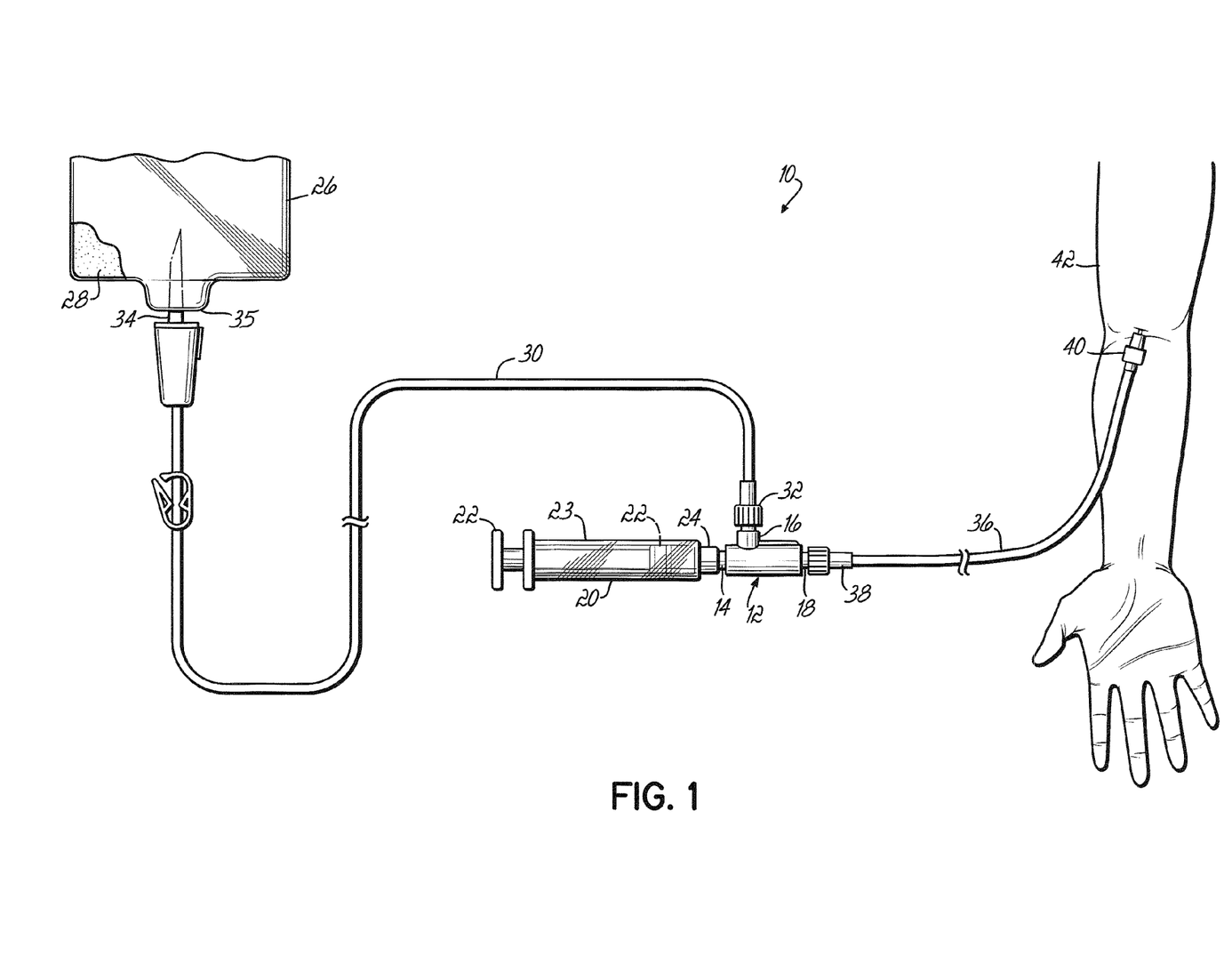
FIG. 1 schematically illustrates a medical dispensing system, for dispensing a fluid intravenously to a patient, that incorporates a shuttle valve in accordance with the principles of the present invention.

Referring now the drawings, FIG. 1 illustrates a system 10 for dispensing medical fluids intravenously to a patient, with system 10 incorporating a shuttle valve 12 according to a first embodiment of the present invention. The shuttle valve 12 includes a common port 14, an inlet port 16 and an outlet port 18. The fluid dispensing system 10 further includes a syringe 20 coupled to the common port 14. The syringe 20 includes a plunger 22 translatable within a barrel 23 integral at the outlet end with a collar 24 coupled to the common port 14 as subsequently discussed in greater detail.

System 10 further includes a source of fluid to be dispensed which can comprise a bag 26, commonly referred to as an IV bag, containing a fluid 28 therein. The fluid 28 can comprise a variety of medications and can also include other fluids, such as saline solution, as is known in the art. The system 10 further includes a first section of tubing 30 that can comprise a single piece of tubing or multiple pieces of interconnected tubing. Tubing 30 is coupled at one end to the inlet port 16 of shuttle valve 12 via connector 32 and terminates at the opposite end in a spike 34 adapted to pierce a port 35 of the IV bag 26, allowing fluid 28 to flow within the tubing 30 to the inlet port 16 of valve 12.

System 10 also includes a second section of tubing 36 that can comprise a single piece of tubing or multiple pieces of interconnected tubing. Tubing 36 is coupled at one end to the outlet port 18 of valve 12 via connector 38 and terminates at an opposite end in a catheter 40 inserted intravenously in an arm 42 of a patient.

Referring now to FIGS. 2-5, the shuttle valve 12 is illustrated in further detail. Valve 12 includes a body 44 defining an interior chamber 46 (FIGS. 3A and 3B), and also includes the common port 14, inlet port 16 and outlet port 18. Each of the ports 14, 16 and 18 are coupled to body 44. The valve 12 further includes a shuttle 48 translatably disposed within the chamber 46 between a first position illustrated in FIG. 3A where the inlet port 16 and common port 14 are fluidically coupled and the common port 14 and outlet port 18 are fluidically uncoupled, and a second position shown in FIG. 3B where the common port 14 and outlet port 18 are fluidically coupled and the common port 14 and inlet port 16 are fluidically uncoupled. The inlet port 16 and outlet port 18 are fluidically uncoupled, regardless of the position of shuttle 48 within chamber 46. The particular manner in which the various ports are either fluidically coupled or uncoupled is subsequently discussed further in greater detail.

Figure 2:
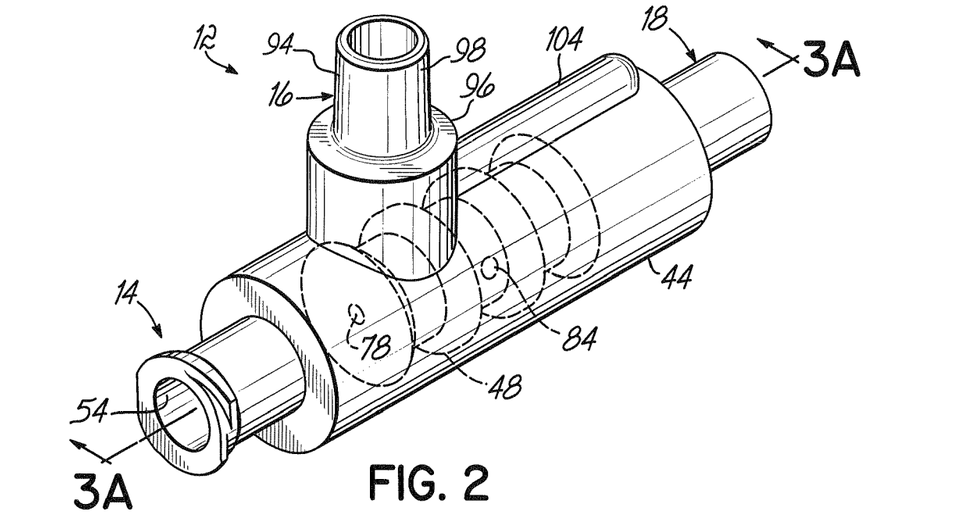
FIG. 2 is an isometric view further illustrating the shuttle valve shown in FIG. 1, according to a first embodiment of the present invention.
Figure 3A:
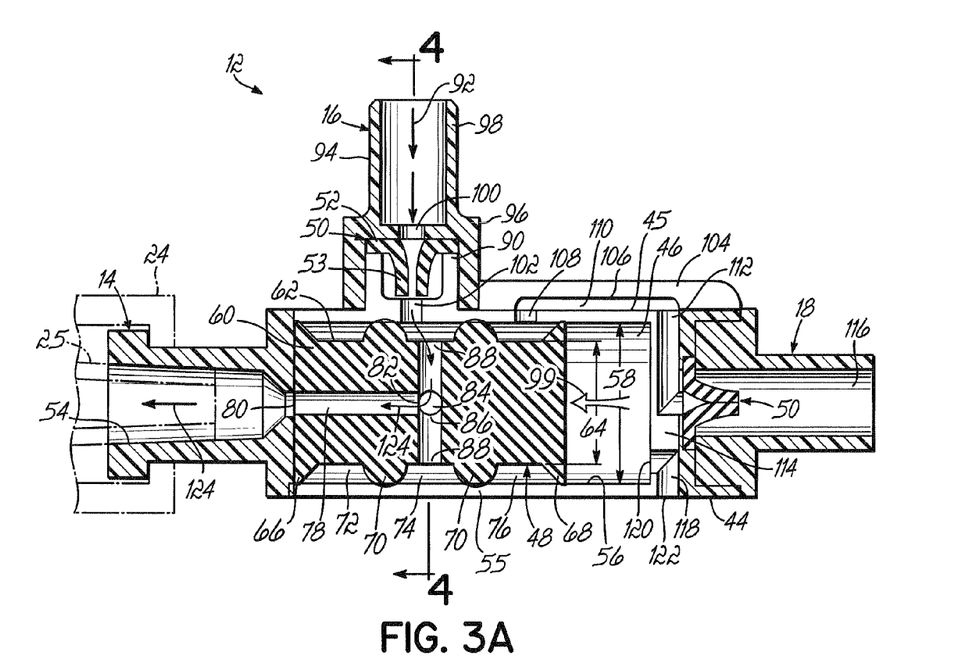
FIG. 3A is a cross-sectional view taken along line 3A-3A in FIG. 2, illustrating the shuttle valve in a first position.
Figure 3B:
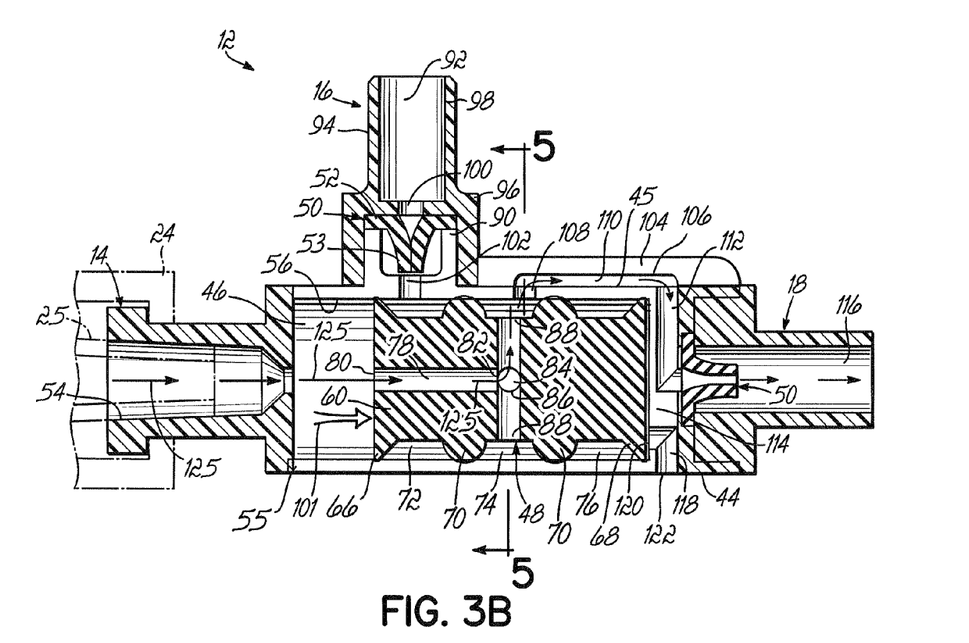
FIG. 3B is a cross-sectional view similar to FIG. 3A, but with the shuttle valve shown in a second position.
Figure 4:
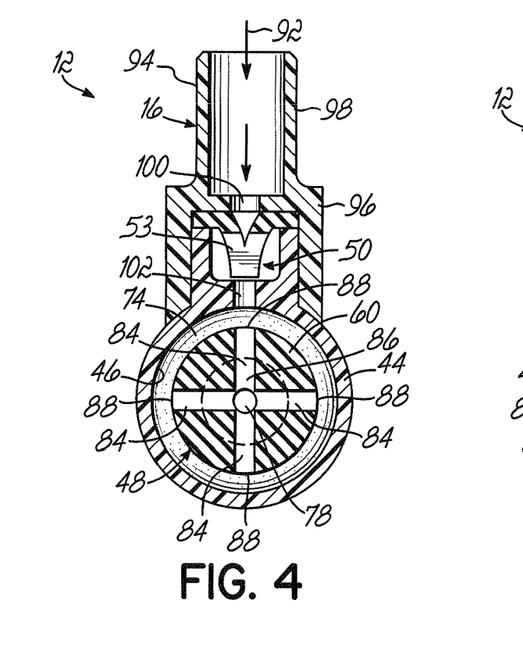
FIG. 4 is a cross-sectional view taken along line 4-4 in FIG. 3A.

The shuttle valve 12 further includes a pair of check valves 50. One of the check valves 50 is coupled to the inlet port 16 in a manner to permit fluid flow through the inlet port 16 into the interior chamber 46 and to prevent fluid from discharging from the chamber 46 through the inlet port 16. The other check valve 50 is coupled to the outlet port 18 in a manner to permit fluid to discharge from the interior chamber 46 through the outlet port 18 and to prevent fluid from flowing through the outlet port 18 into the chamber 46.

The common port 14 comprises a female Luer lock coupling having an internal passage 54 with a shape that is complimentary to the shape of the Luer taper 25 at the distal end of a conventional syringe 20, and the collar 24 of the syringe 20 can be locked onto the Luer lock coupling 14 as shown in phantom line FIGS. 3A and 3B.

The body 44 of the shuttle valve 12 has a substantially cylindrical wall 55 with an inner surface 56 having a diameter 58. The shuttle 48 has a body portion 60 with a substantially cylindrical outer surface 62 having a diameter 64 that is less than the diameter 58 of the inner surface 56 of the body 44 of shuttle valve 12. Shuttle 48 further includes a plurality of longitudinally spaced, annular seals extending outwardly from the body portion 60 and comprising first 66 and second 68 terminal end seals having a generally conical shape and a pair of annular seals 70 disposed intermediate of the terminal end seals 66, 68. The seals 66, 68 and 70 are disposed in slidable, sealing engagement with the inner surface 56 of the body 44 of shuttle valve 12. Seals 66, 68 and 70, together with the inner surface 56 of body 44 and the outer surface 60 of shuttle 48, define first 72, second 74 and third 76 annular cavities that are translatable with the shuttle 48 within the interior chamber 46 of shuttle valve 12. The second cavity 74 is disposed intermediate cavities 72 and 76 and is generally centrally disposed on shuttle 48.

The body 44 of shuttle valve 12 can be made of a rigid plastic material such as a polycarbonate or PVC. The body portion 60 of shuttle 48 can be made of a bio-compatible plastic with the seals 66, 68 and 70 made of an elastomeric material and bonded to the body portion 60. Alternatively, the body portion 60 and seals 66, 68 and 70 can be integrally formed from an elastomeric material.

Shuttle 48 further includes a longitudinally extending passage 78 that has a proximal end 80 fluidically coupled with the common port 14 and, more particularly, with the passage 54 of common port 14. The syringe 20 is not shown within passage 54 in FIGS. 3A and 3B for purposes of illustration. However, when the syringe 20 is disposed within passage 54, the proximal end 80 of the longitudinally extending passage 78 is fluidically coupled to the interior (not shown) of the syringe 20. The longitudinally extending passage 78 also includes a distal end 82 terminating within the body portion 60 of shuttle 48. Shuttle 48 further includes a plurality of radially extending passages 84, with each of the passages 84 fluidically coupled, at a proximal end 86 (FIGS. 4 and 5) thereof, with the distal end 82 of longitudinally extending passage 78. A distal end 88 of each of the passages 84 opens onto the external surface 62 of the body portion 60 of shuttle 48. Accordingly, the common port 14 is in fluid communication with, or is fluidically coupled with, the second annular cavity 74, regardless of the position of the shuttle 48 within the interior chamber 46.

The inlet port 16 comprises a hollow cylinder 90 that protrudes away from the cylindrical wall 55 of body 44 of shuttle valve 12. An outer edge of the cylinder 90 provides a shoulder to support a flange portion 52 of the check valve 50 disposed within the inlet port 16. The check valve 50 is in series fluidically with the inlet port 16 and a converging portion 53 of the check valve 50 is disposed within a hollow interior of cylinder 90. Check valves 50 are preferably made of an elastomeric material and are sometimes referred to as "duckbilled" check valves due to the shape of the converging portion 53 of valves 50. As fluid enters a central opening formed in the flange 52 of valve 50, such as fluid traveling in the direction indicated by flow arrows 92 in FIG. 3A, the converging portion 53 of the elastomeric check valve 50 is forced open, allowing flow through the check valve 50 in the direction corresponding to flow arrows 92. When fluid pressure is released, the converging portion closes and prevents flow in an opposite direction. Accordingly, the check valve 50 disposed in inlet port 16 prevents fluid from flowing from the interior chamber 46 outward through the inlet port 16.

Inlet port 16 further includes a tube coupling 94 having a relatively larger diameter inner cylindrical portion 96 and a relatively smaller diameter outer cylindrical portion 98 integral with the inner cylindrical portion 96. A hollow interior of the inner cylindrical portion 96 is disposed in surrounding and contacting relationship with the cylinder 90 that protrudes from the cylindrical wall 55 of body 44 of shuttle valve 12. As shown in FIGS. 3A and 3B, the outer cylindrical portion 98 includes an end wall with an opening 100 formed therein that communicates with check valve 50. An opening 102 is formed in an end wall of cylinder 90, with opening 102 fluidicly coupled with the outlet of check valve 50 and with the interior chamber 46.

A member 104 extends longitudinally away from the inner cylindrical portion 96 of tube coupling 94. An outlet passage 106 is fluidicly coupled with both the interior chamber 46 and the outlet port 18. The outlet passage 106 includes an opening 108 extending through the cylindrical wall 55 of body 44, a longitudinally extending portion 110 that extends along an outer surface 45 of wall 55 of body 44 and an inwardly extending portion 112 that extends through a transverse end wall 114 of the body 44 of shuttle valve 12 and is fluidicly coupled with the check valve 50 disposed within the outlet port 18.

Figure 5:
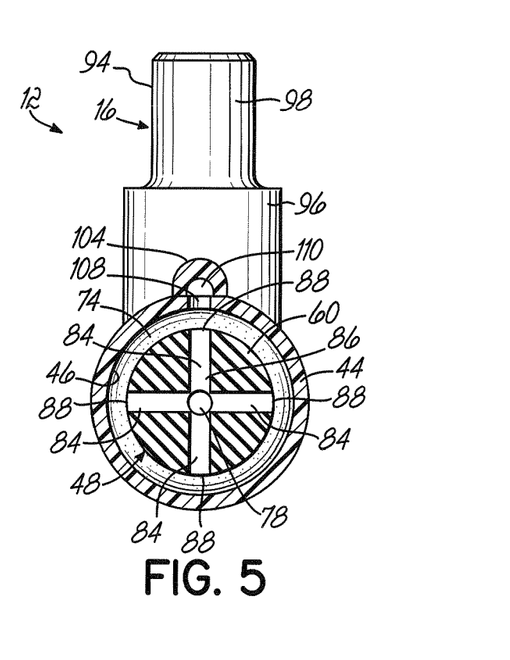
FIG. 5 is a cross-sectional view taken along line 5-5 in FIG. 3B.

As shown in FIG. 5, the portion 110 of the outlet passage 106 comprises a recess formed in the member 104. The outlet port 18 comprises a tube coupling coupled to body 44. In the illustrative embodiment, the outlet port 18 is configured to engage the cylindrical wall 55 and transverse wall 114 of the body 44 of shuttle valve 12 and is secured thereto by conventional means such as ultrasonic welding or bonding. The outlet port 18 has a hollow interior 116 with the check valve 50 disposed therein and can be coupled to connector 38 at the end of tubing section 36 shown in FIG. 1. The check valve 50 is in series fluidicly with the outlet port 18.

The shuttle valve 12 further includes a vent passage 118 having a first end 120 that is fluidicly coupled with the interior chamber 46 of body 44 of valve 12 and a second end 122 that opens onto the outer surface 45 of wall 55 of body 44. Accordingly, a portion of the interior chamber 46 is vented to the atmospheric pressure which exists exterior of valve 12, via the vent passage 118.

In operation, when a caregiver wishes to administer fluid 28 to the patient, the caregiver initially retracts the plunger 22 of syringe 20 to draw fluid 28 into syringe 20. Prior to this action, the shuttle 48 will typically be in the position shown in FIG. 3B, as a result of a previous dose of fluid 28 being administered to the patient. As a result of the caregiver withdrawing or retracting the plunger 22, a reduced fluid pressure, relative to atmospheric pressure, exists at the common port 14 and within a portion of the interior chamber 46 proximate the common port 14. The presence of one of the check valves 50 disposed in series fluidicly with outlet port 18 allows this reduced pressure to exist. The vent passage 118 vents a portion of the interior chamber 46 to atmospheric pressure. More particularly, the portion of chamber 46 between the outlet port 18 and the shuttle 48 is vented to atmospheric pressure. Since this pressure is greater than the reduced pressure or slight vacuum existing at the common port, a differential pressure is created across shuttle 48 causing shuttle 48 to move toward the common port 14 as indicated by arrow 99. The force causing shuttle 48 to move toward common port 14 acts on an end surface of shuttle 48 that includes terminal end seal 68. The existence of terminal end seal 68 and the adjacent annular seal 70, allow the foregoing pressure differential to exist within interior chamber 46.

When the shuttle 48 is disposed against the common port 14, as shown in FIG. 3A, the outlet port 18 is fluidicly coupled with the annular cavity 76 that is sealed from the remainder of the interior chamber 46 via terminal end seal 68 and the adjacent annular seal 70. Accordingly, the outlet port 18 is fluidicly uncoupled from the common port 14 and the inlet port 16 with the shuttle 48 in this position.

Once the shuttle 48 has moved all the way to the common port 14 as shown in FIG. 3A, the partial vacuum that exists at the common port 14 also exists within the longitudinally extending passage 78 and the radially extending passages 84, with this vacuum communicated through annular cavity 74 and opening 102 into the interior of cylinder 90, which causes check valve 50 to open, in conjunction with the positive pressure of the fluid 28 flowing within the cylindrical portions 98 and 96 along flow arrows 92. Fluid 28 then passes through check valve 50, opening 102, radially extending passages 84 and the longitudinally extending passage 78 into the syringe 20 (not shown in FIGS. 3A and 3B) disposed within the interior passage 54 of common port 14 as indicated by flow arrows 124.

When the caregiver advances the plunger 22 of syringe 20 to administer fluid 28 to the patient, a positive pressure is created at the common port 14 which is greater than the atmospheric pressure which exists between shuttle 48 and the outlet port 18. The presence of one of the check valves 50 disposed in series fluidicly with inlet port 16 allows this positive pressure to exist. Accordingly, the shuttle 48 is pushed toward the outlet port 18, as indicated by arrow 101. When the shuttle 48 is disposed in contacting engagement with wall 114 or in close proximity to wall 114 as shown in FIG. 3B, the inlet port 16 is fluidicly coupled with the annular cavity 72 that is sealed from the remainder of the interior chamber 46 via terminal end seal 66 and the adjacent annular seal 70. Accordingly, the inlet port 16 is fluidicly uncoupled from the common port 14 and the outlet port 18 with the shuttle 48 in this position.

With the shuttle 48 in the position shown in FIG. 3B, fluid 28 is expelled out of the syringe 20 into the interior chamber 46, through the longitudinally extending passage 78 and the radially extending passages 84 and into the annular cavity 74, bounded on either side by one of the annular seals 70 as indicated by flow arrows 125. Fluid 28 then flows through the opening 108 formed in the cylindrical wall 55 of the body 44 of valve 12, then through portions 110 and 112 of the outlet passage 106, through check valve 50 and into the interior portion 116 of the outlet port 18. From there, the fluid can flow through the tubing section 36 into the arm 42 of the patient, as shown in FIG. 1.

Figure 6A:
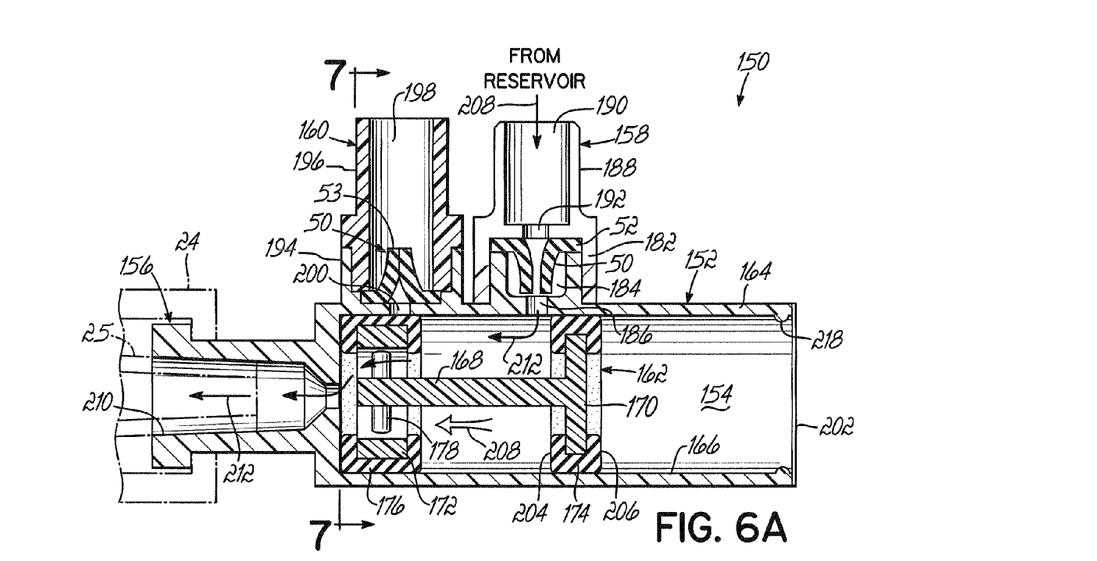
FIG. 6A is a cross-sectional view illustrating a second shuttle valve in accordance with the principles of the present invention, with the valve shown in a first position.
Figure 6B:
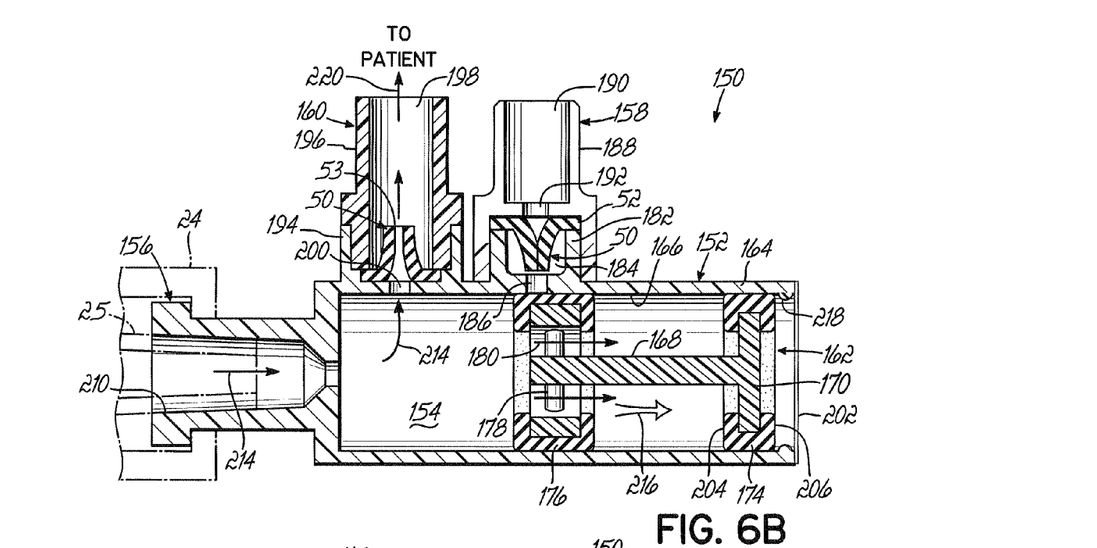
FIG. 6B is a cross-sectional view similar to FIG. 6A, but with the valve shown in a second position.
Figure 7:
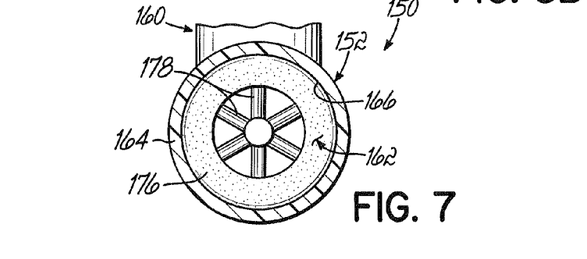
FIG. 7 is a cross-sectional view taken along line 7-7 in FIG. 6A.

FIGS. 6A, 6B and 7 illustrate a shuttle valve 150 according to a second embodiment of the present invention. Shuttle valve 150 includes a body 152 defining an interior chamber 154, and also includes a common port 156, an inlet port 158 and an outlet port 160. Each of the ports 156, 158 and 160 are coupled to body 152. Shuttle valve 150 further includes a shuttle 162 translatably disposed within the chamber 154 between a first position shown in FIG. 6A, where the inlet port 158 and the common port 156 are fluidicly coupled and the common port 156 and the outlet port 160 are fluidicly uncoupled, and a second position shown in FIG. 6B, where the outlet port 160 and the common port 156 are fluidicly coupled and the common port 156 and the inlet port 158 are fluidicly uncoupled. The inlet port 158 and the outlet port 160 are fluidicly uncoupled in both positions of shuttle 162.

The shuttle valve 150 further includes a pair of check valves 50 discussed previously with respect to shuttle valve 12. As discussed previously, each of the check valves 50 include a flange portion 52 and a converging portion 53, extending away from the flange portion 52. One of the check valves 50 is disposed within the inlet port 158 and is in series fluidicly with inlet port 158, while the other check valve 50 is disposed within the outlet port 160 and is in series fluidicly with outlet port 160. The series relationship of these check valves 50 with the inlet 158 and outlet 160 ports allow either a reduced pressure or positive pressure to exist at the common port 156 as discussed previously with respect to shuttle valve 12. The shuttle 162 is responsive to varying a fluid pressure at the common port 156 to move between the first and second positions shown in FIGS. 6A and 6B, respectively. More particularly, the shuttle 162 is movable into the first position shown in FIG. 6A, in response to decreased fluid pressure at the common port 156, relative to atmospheric pressure, and is movable into the second position shown in FIG. 6B, in response to increased fluid pressure at the common port, relative to atmospheric pressure.

The body 152 of the shuttle valve 150 has a substantially cylindrical wall 164 with an inner surface 166. The shuttle 162 includes a longitudinally extending stem 168, a disk 170 integral with one end of the stem 168 and an annular member 172 interconnected to the stem 168 proximate an opposite end thereof. The disk 170 and the annular member 172 are slidably sealed with the inner surface 166 of the substantially cylindrical wall 164 via annular seals 174 and 176, respectively. Seal 174 is disposed about a periphery of disk 170 while seal 176 is disposed about a periphery of annular member 172. The body 152 of shuttle valve 150 can be made of a rigid plastic material such as a polycarbonate or PVC. The stem 168, disk 170 and annular member 172 of shuttle 162 can be made of a bio-compatible plastic, while the seals 174 and 176 can be made of an elastomeric material.

The shuttle 162 further includes a plurality of circumferentially spaced, radially extending spokes 178 (best shown in FIG. 7) that are integral with, and extend between, the stem 168 and the annular member 172. The circumferentially spaced spokes 178 permit the common port 156 and the disk 170 to be fluidicly coupled, as illustrated by flow arrows 180 in FIG. 6B.

The inlet port 158 comprises a cylinder 182 integral with the substantially cylindrical wall 164 of body 152 of valve 150 and extending away from wall 164. An outer edge of the cylinder 182 acts as a shoulder to support the flange portion 52 of the check valve 50 disposed within the inlet port 158. The converging portion 53 of check valve 50 is disposed within a hollow interior 184 of cylinder 182. The inlet port 158 further includes an aperture 186 formed in the cylindrical wall 164 of body 152 that communicates with the interior chamber 154 and the hollow interior 184 of cylinder 182. The inlet port 158 also includes a tube coupling 188 having a hollow inner portion disposed in surrounding and engaging relationship with the cylinder 182 and a hollow outer portion defining an inlet passage 190. An aperture 192 is formed in an intermediate wall of the coupling 188 and communicates with the hollow interior 190, the hollow interior 184 and check valve 50. Coupling 188 can be coupled to the connector 32 at one end of the tubing section 30 shown in FIG. 1.

The outlet port 160 includes a hollow cylinder 194 integral with the substantially cylindrical wall 164 of body 152 and protruding outwardly from wall 164 and a tube coupling 196 having a lower portion disposed within a hollow interior of cylinder 194. Tube coupling 196 defines an interior passage 198 and can be coupled to the connector 38 at one end of the tubing section 36 shown in FIG. 1. One of the check valves 50 is disposed within the outlet port 160 as shown in FIGS. 6A and 6B. More particularly, the flange portion 52 of the check valve 50 is disposed within a recess formed in the cylinder 194 and the converging portion 53 extends into the passage 198. The outlet port 160 further includes an aperture 200 that extends through the cylindrical wall 164 of the body 152 of valve 150 and is fluidicly coupled with the interior chamber 154 of body 152 as well as the passage 198 and check valve 50.

The common port 156 can be integrally formed with body 152 as shown in FIGS. 6A and 6B. Alternatively, one end of the cylindrical wall 164 of the body 152 of shuttle valve 150 is secured, by conventional means such as ultrasonic welding, to the common port 156 which comprises a female Luer lock fitting in the illustrative embodiment. The opposite end of the cylindrical wall 164 is substantially open to the atmosphere exterior of shuttle valve 150. The shuttle valve 150 optionally includes a fine mesh screen 202 that is secured to the end of the cylindrical wall 164 opposite the common port 156, with the filter 202 being effective for preventing bacteria from entering the interior chamber 154. The substantially open end of body 152 is effective for venting the portion of the interior chamber 154 that exists between filter 202 and shuttle 162, to atmospheric pressure. The sealing engagement of disk 170 with the inner surface 166 of cylindrical wall 164, created by seal 174, prevents the remainder of chamber 154 from being vented to atmosphere.

In operation, when a caregiver wishes to administer fluid 28 to the patient, the caregiver initially retracts the plunger 22 of syringe 20 (shown in FIG. 1) to draw fluid 28 into syringe 20. This results in a decreased pressure, relative to atmospheric pressure, to exist in the interior chamber 154 at the common port 156 and between the common port 156 and a side 204 of the seal 174 which faces the common port 156. The decreased pressure can be communicated to the portion of the interior chamber 154 that exists between seals 174 and 176, due to the spaces which exist between the radially extending and circumferentially spaced spokes 178. Atmospheric pressure acts on an opposite side 206 of seal 176, so that a pressure differential exists across the seal 176 which forces the shuttle 162 to move toward the common port 156 as indicated by arrow 208 in FIG. 6A. The shuttle continues movement in this direction until it contacts the common port 156. The combination of the suction or decreased pressure that exists within the interior chamber 154 between seals 174 and 176, in combination with the pressure of the fluid 28 flowing through passage 190 as indicated by flow arrow 208, and through aperture 192 and into the hollow interior 184 of cylinder 182, acts to open the check valve 50 disposed within the inlet port 158. The fluid 28 then flows through aperture 186 into the interior chamber 154, through the spaces between radially extending spokes 178 and into the syringe 20 disposed in passage 210 of the common port 156, as indicated by flow arrows 212 (the syringe 20 is not shown in passage 210 for purposes of illustration). With the shuttle 162 in the position shown in FIG. 6A, the annular seal 176 closes the outlet port 160 thereby causing the outlet port 160 to be fluidicly uncoupled from both the common port 156 and the inlet port 158.

When the caregiver wants to administer the fluid 28 to the patient, such as intravenously into the arm 42 of the patient as shown in FIG. 1, the caregiver advances the plunger 22 of syringe 20. This causes the fluid 28 to be discharged from the syringe 20 into the interior chamber 154, as indicated by flow arrows 214 in FIG. 6B. This also causes an increase in fluid pressure at the common port 156 and within the interior chamber 154 between the common port 156 and side 204 of seal 174. Again, atmospheric pressure acts on side 206 of seal 174 so that a pressure differential exists across seal 174. However, in this case, the pressure differential is such that a force acts on side 204 of seal 174 so that the shuttle 162 moves away from the common port 156 as shown by arrow 216 in FIG. 6B. The shuttle 162 continues to move in direction 216 until seal 174 contacts one or more stops 218 that protrude inwardly from the inner surface 166 of the substantially cylindrical wall 164 of body 152 of valve 150, as shown in FIG. 6B. In this position, the seal 176 closes the inlet port 158, thereby causing the inlet port 158 to be fluidicly uncoupled from both the common port 156 and the outlet port 160.

After the fluid 28 flows into the interior chamber 154, it flows through aperture 200 and check valve 50 with the pressure of fluid 28 opening check valve 50. The fluid 28 then flows through passage 198 as shown by flow arrows 220 and can be delivered to the patient via tubing 36 and needle 40 as shown in FIG. 1.

Figure 8A:
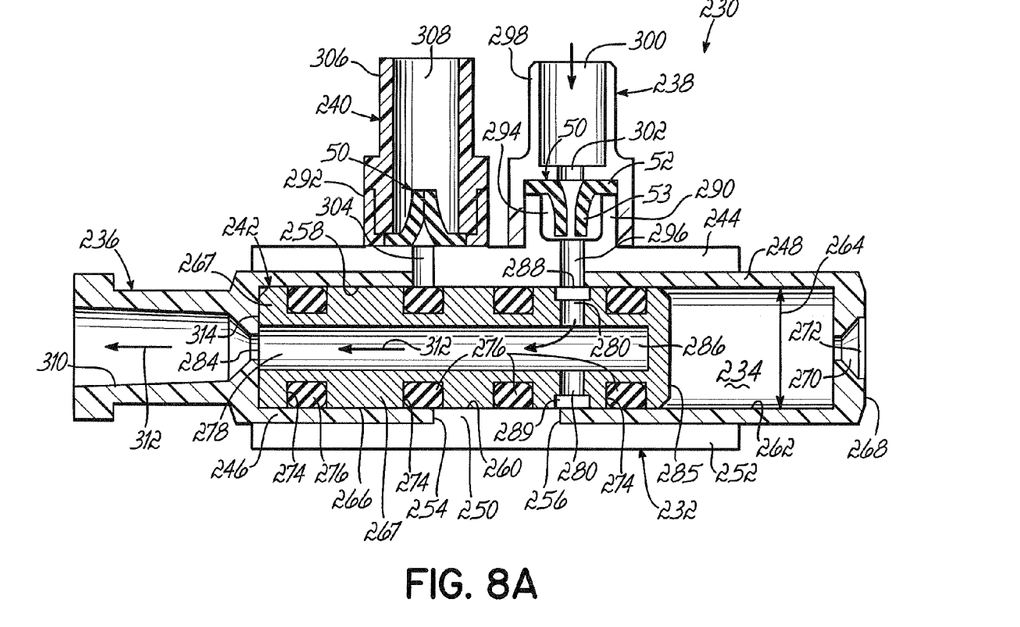
FIG. 8A is a cross-sectional view illustrating a third shuttle valve in accordance with the principles of the present invention, with the valve shown in a first position.
Figure 8B:
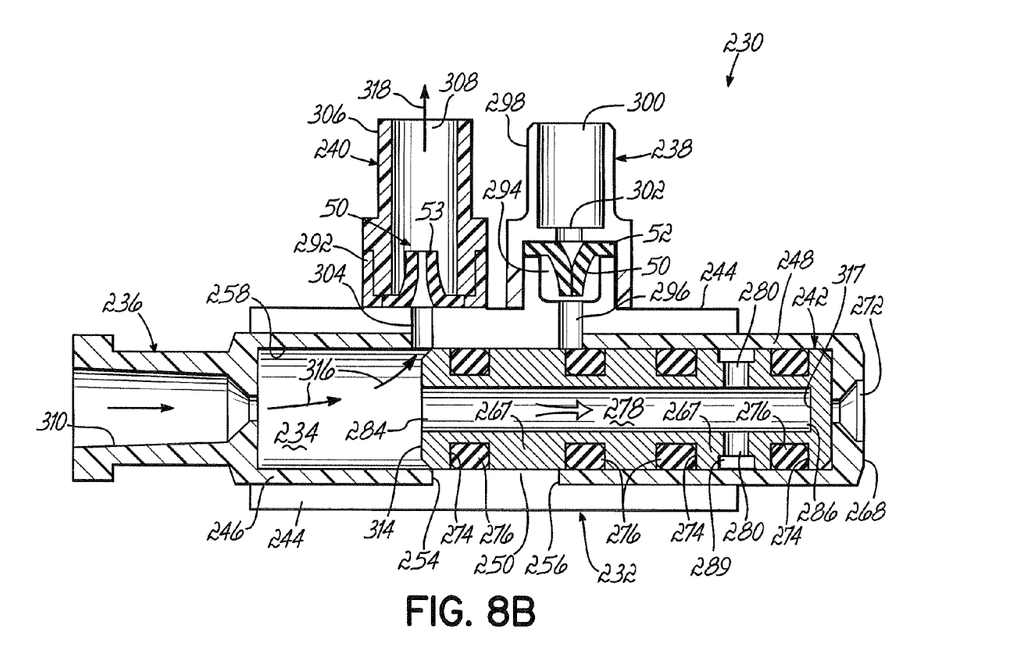
FIG. 8B is a cross-sectional view similar to FIG. 8A but with the valve shown in a second position.

FIGS. 8A and 8B illustrate a shuttle valve 230 according to a third embodiment of the present invention. Shuttle valve 230 includes a body 232 defining an interior chamber 234, and also includes a common port 236, an inlet port 238 and an outlet port 240. Each of the ports 236, 238 and 240 is coupled to body 232. The shuttle valve 230 further includes a shuttle 242 translatably disposed within the chamber 234 between a first position shown in FIG. 8A, wherein the inlet port 238 and the common port 236 are fluidicly coupled and the common port 236 and the outlet port 240 are fluidicly uncoupled, and a second position shown in FIG. 8B, wherein the outlet port 240 and the common port 236 are fluidicly coupled and the common port 236 and the inlet port 238 are fluidicly uncoupled.

Shuttle valve 230 also includes a pair of the check valves 50 discussed with respect to previous embodiments of the present invention. A first one of the check valves 50 is coupled to the inlet port 238 in a manner to permit fluid flow through the inlet port 238 into the chamber 234 and to prevent fluid from discharging from the chamber 234 through the inlet port 238. The second check valve 50 is coupled to the outlet port 240 in a manner to permit fluid to discharge from the chamber 234 through the outlet port 240 and to prevent fluid from flowing through the outlet port 240 into the chamber 234. The first check valve 50 is disposed within the inlet port 238 and is in series fluidicly with the inlet port 238, while the second check valve 50 is disposed within the outlet port 240 and is in series fluidicly with outlet port 240. The series relationship of these check valves 50 with the inlet 238 and outlet 240 ports allow either a reduced pressure or positive pressure to exist at the common port 236 as discussed previously with respect to shuttle valve 12.

As discussed subsequently in greater detail, the shuttle 242 is responsive to varying a fluid pressure at the common port 236 to move between the first and second positions. More particularly, the shuttle 242 is movable into the second position in response to increased fluid pressure at the common port 236 and is movable into the first position in response to decreased fluid pressure at the common port 236.

The body 232 of the shuttle valve 230 includes first 244, second 246 and third 248 substantially cylindrical portions. The second substantially cylindrical portion 246 is substantially disposed within the first portion 244 and is integrally formed in the illustrative embodiment with the common port 236. Alternatively, the common port 236 can be separately formed and secured to body 232 by conventional means such as bonding. The third substantially cylindrical portion 248 of the body 232 is disposed partially within the first portion 244, and protrudes longitudinally away from the first portion 244 as shown in FIGS. 8A and 8B to accommodate the length of shuttle 242 when shuttle 242 is in the position shown in FIG. 8B. The first portion 244 of the body 232 includes a generally centrally disposed shoulder 250 protruding inwardly from a remaining portion 252 of the first portion 244. The second portion 246 of body 232 includes an open end 254 for accepting shuttle 242 therethrough, with the open end 254 being disposed in abutting relationship with the shoulder 250. Similarly, the third portion 248 of body 232 includes an open end 256 for accepting shuttle 242 therethrough, with the open end 256 also being disposed in abutting relationship with the shoulder 250. The body 232 of valve 230 includes an inner surface comprising an inner surface 258 of the second portion 246 of body 232, an inner surface 260 of shoulder 250, and an inner surface 262 of the third portion 248 of body 232. The inner surface of the body 232 has a diameter 264 which is substantially the same as a diameter of a substantially cylindrical outer surface 266 of a body portion 267 of shuttle 242.

The third portion 248 of body 232 includes a transverse wall 268 at an end opposite the open end 256 and a vent passage 270 formed therethrough. The vent passage 270 communicates with the interior chamber 234 and the atmosphere exterior of valve 230. The valve 230 may optionally include a filter 272 secured to the third portion 248 over one end of the vent passage 270. The filter 272 can comprise a fine mesh screen filter effective for keeping bacteria out of the interior chamber 234.

The shuttle 242 includes a plurality of longitudinally spaced annular recesses 274 formed in the outer surface 266 of shuttle 242. Valve 230 further includes a plurality of elastomeric seals 276, with each of the seals 276 being disposed in one of the annular recesses 274 of shuttle 242. Each of the seals 276 are substantially flush with the outer surface 266 of shuttle 242 and are disposed in slidable, sealing engagement with the inner surface of the body 232 of the shuttle valve 230. The configuration of the first 244, second 246 and third 248 substantially cylindrical portions of body 232, in combination with the positioning of seals 276 within recesses 274, helps maintain the structural integrity of the seals 276 as the shuttle moves between the positions shown in FIGS. 8A and 8B. The body 232 of shuttle valve 230 can be made of a rigid plastic material such as a polycarbonate or PVC. The body portion 267 of shuttle 242 can be made of a bio-compatible plastic material.

The shuttle 242 further includes a longitudinally extending passage 278 and a plurality of radially extending passages 280 disposed within the body portion 267 of the shuttle 242. Shuttle 242 may include six of the radially extending passages 280 (only two shown in FIGS. 8A and 8B), with the passages 280 equally spaced circumferentially as illustrated with respect to passages 278 of shuttle 252 illustrated in FIG. 7. Alternatively, shuttle 242 may include a different number of passages 280. The longitudinally extending passage 278 is fluidicly coupled at an end 284 with the common port 236 and is fluidicly coupled with the radially extending passages 280 at a location proximate an opposite end 286 of the passage 278. Each of the radially extending passages 280 have a distal end 288 that opens onto the outer surface 266 of the body portion 267 of shuttle 242, and is fluidicly coupled with an annular cavity 289 formed in the body portion 267.

The inlet port 238 comprises a hollow cylinder 290 which extends away from the first substantially cylindrical portion 244 of body 232. Cylinder 290 includes an outer edge that acts as a shelf supporting a flange portion 52 of the check valve 50 disposed within the inlet port 238, with the converging portion 53 of check valve 50 being disposed within a hollow interior 294 of the cylinder 290. The inlet port 238 further includes an aperture 296 formed in body 232 that is fluidically coupled with the hollow interior 294 of cylinder 290 at one end thereof and opens onto the inner surface of body 232 at the other end thereof. When shuttle 242 is in the first position shown in FIG. 8A, aperture 296 is fluidically coupled with the common port 236 via the radially extending passages 280 and the longitudinally extending passage 278.

Inlet port 238 further includes a coupling 298 having an inner cylindrical portion disposed in surrounding relationship with the cylinder 290. Coupling 298 defines an interior passage 300 and includes an aperture 302 formed in an intermediate wall of the coupling. Passage 300 is fluidically coupled with aperture 302, which in turn, is fluidically coupled with the check valve 50 and the hollow interior 294 of cylinder 290. Coupling 298 can be coupled to connector 32 at one end of the tubing section 30 shown in FIG. 1.

The outlet port 240 comprises an aperture 304 formed in body 232 that opens onto the inner surface of the body 232. Accordingly, when the shuttle 242 is in the position shown in FIG. 8B, aperture 304 is fluidically coupled with the interior chamber 234 and the common port 236. The outlet port 240 further comprises a cylinder 292 which is integral with and extends away from the first substantially cylindrical portion 244 of body 232 and one of the check valves 50 which is disposed within a hollow interior of the cylinder 292. The outlet port 240 further comprises a tube coupling 306 which is suitable for mating with a female coupling such as coupling 38 attached to one end of tubing section 36 which is coupled at the opposite end to a patient's arm 42 as shown in FIG. 1. Coupling 306 defines an interior passage 308.

In operation, when a caregiver wishes to administer a fluid such as fluid 28 to the patient, the caregiver initially retracts plunger 22 of syringe 20 (not shown in FIGS. 8A and 8B) to draw fluid 28 into syringe 20. Prior to this action, the shuttle 242 will typically be in the position shown in FIG. 8B, as a result of a previous dose of fluid 28 being administered to the patient. As a result of the caregiver withdrawing or retracting the plunger 22, a reduced fluid pressure, relative to atmospheric pressure, exists at the common port 236 and within the longitudinally extending passage 278 and the radially extending passages 280 within shuttle 242. Reduced pressure also exists within the interior chamber 234 proximate the common port 236. The vent passage 270 is effective for communicating atmospheric pressure against an end surface 285 of shuttle 242 adjacent the vent passage 270 and, as the shuttle moves, within the portion of the interior chamber 234 between shuttle 242 and vent passage 270. Accordingly, a differential pressure is created across shuttle 242 causing shuttle 242 to move toward the common port 236 and to eventually be disposed in abutting relationship with the common port 236 as shown in FIG. 8A. The existence of the elastomeric seals 276 disposed in sealing engagement with the inner surface of body 232 allows this differential pressure to exist within the interior chamber 234, across shuttle 242. Once the shuttle 242 has moved all the way to the common port 236 as shown in FIG. 8A, the partial vacuum that exists at the common port 236 and within the longitudinally extending passage 278 and the radially extending passages 280, will also exist within the aperture 296 and the interior 294 of cylinder 290. This reduced pressure causes check valve 50 to open, in conjunction with the positive pressure of the fluid 28 flowing within passage 300, aperture 302 and into the hollow interior 294 of cylinder 290. Fluid 28 then passes through the open check valve 50, aperture 296, annular cavity 289, each one of the radially extending passages 280 and the longitudinally extending passage 278 into the syringe 20 (not shown in FIGS. 8A and 8B) which is disposed within an interior 310 of the common port 236, as indicated by flow arrows 312. In the position shown in FIG. 8A, the shuttle 242 closes the outlet port 240 so it is fluidically uncoupled from the common port 236 and the inlet port 238.

When the caregiver advances the plunger 22 of syringe 20 to administer fluid 28 to the patient, positive pressure is created at the common port 236 and within the longitudinally extending passage 278, the radially extending passages 280 and the aperture 296. This causes the check valve 50 disposed within the inlet port 238 to close and creates forces acting on an end surface 314 of shuttle 242 and on an inner surface 317 of shuttle 242 located adjacent a distal end of the longitudinally extending passage 278. A pressure differential is created across shuttle 242 in view of the atmospheric pressure existing in the portion of the interior chamber between shuttle 242 and the vent passage 270. The forces acting on the end surface 314 and inner surface 317 of the shuttle 242, causes the shuttle 242 to move away from the common port until it abuts the transverse wall 268 of the third portion 248 of body 232 of valve 230, as shown in FIG. 8B. With the shuttle 242 in this position, the inlet port 238 is closed due to the proximity of shuttle 242 with aperture 296 and the annular seals 276 that exist on either side of aperture 296. Accordingly, the inlet port 238 is fluidically uncoupled from the common port 236 and the outlet port 240. With the shuttle 242 in the position shown in FIG. 8B, fluid 28 can flow into the interior chamber 234 and into the aperture 304 of outlet port 240 as shown by flow arrows 316. The positive pressure of the fluid 28 opens the check valve 50 disposed within the outlet port 240. The fluid then flows into the interior passage 308 as shown by flow arrow 318 and then through the tubing section 36 into the arm 42 of the patient.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For instance, in some environments, the shuttle valve can incorporate a spring to bias the shuttle into an initial position. Additionally, while the shuttle valves of the present invention have been described for use in a fluid dispensing system, such as system 10 illustrated in FIG. 1, where a caregiver retracts the plunger 22 of syringe 20 to fill the syringe 20 with fluid 28 and advances the plunger 22 to expel or discharge the fluid 28 out of syringe 20, the shuttle valves of the present invention can be used in conjunction with a syringe pump. In this case, a caregiver retracts the plunger of the included syringe to fill the syringe with fluid but the syringe pump is used to advance the plunger to expel or discharge the fluid from the syringe. Furthermore, while the inlet and outlet ports of the embodiments, illustrated in the Figures have been shown in the form of tube coupling ports, alternatively they can be female Luer lock coupling ports. The invention in its broader aspects is, therefore, not limited to the specific details, representative apparatus and method, and illustrative examples shown and described. Accordingly, departures may be made from such details without departing from the spirit or scope of the general inventive concept.

What is Claimed is:

1. A shuttle valve comprising:
a body defining an interior chamber;
an inlet port, an outlet port and a common port, each of the ports being coupled to the body;

a shuttle translatably disposed within the chamber between a first position wherein the inlet port and the common port are fluidicly coupled and the common port and the outlet port are fluidicly uncoupled and a second position wherein the outlet port and the common port are fluidicly coupled and the common port and the inlet port are fluidicly uncoupled the shuttle adapted to change position from the first position to the second position and from the second position to the first position solely in response to pressure of fluid intended to be communicated through the common port;

a first check valve coupled to the inlet port in a manner to permit fluid flow through the inlet port into the chamber and to prevent fluid from discharging from the chamber through the inlet port; and a second check valve coupled to the outlet port in a manner to permit fluid to discharge from the chamber through the outlet port and to prevent fluid from flowing through the outlet port into the chamber.

2. The shuttle valve of claim 1, the shuttle being responsive to varying a fluid pressure at the common port to move between the first and second positions.

3. The shuttle valve of claim 1, the shuttle being moveable into the second position in response to increased fluid pressure at the common port.

4. The shuttle valve of claim 1, the shuttle being moveable into the first position in response to decreased fluid pressure at the common port.

5. A shuttle valve as recited in claim 1, wherein:
the first check valve is disposed within the inlet port; and
the second check valve is disposed within the outlet port.

6. A shuttle valve as recited in claim 1, wherein:
the first check valve is disposed in series fluidicly with the inlet port; and
the second check valve is disposed in series fluidicly with the outlet port.

7. A shuttle valve as recited in claim 5, wherein:
the first check valve is made of a first elastomeric material;
the second check valve is made of a second elastomeric material.

8. A shuttle valve as recited in claim 1, wherein:
the body of the shuttle valve is made of a plastic material.

9. A shuttle valve as recited in claim 1, wherein:
the shuttle is made of an elastomeric material.

10. A shuttle valve as recited in claim 1, wherein:
the body portion of the shuttle is made of a plastic material.

11. A shuttle valve as recited in claim 10, wherein:
the shuttle further comprises a plurality of annular seals integral with the body portion and extending outwardly there from; and
the seals are made of an elastomeric material and are secured to the body portion of the shuttle.

12. A shuttle valve as recited in claim 1, wherein:
the body of the shuttle valve has a substantially cylindrical wall with an inner surface;
the shuttle includes a longitudinally extending stem, a disk integral with one end of the stem and including a periphery and an annular member interconnected to the stem proximate an opposite end thereof and including a periphery;
the annular member and the disk are slidably sealed with the inner surface of the substantially cylindrical wall.

13. A shuttle valve as recited in claim 12, wherein:
the common port is secured to one end of the substantially cylindrical wall of the body of the shuttle valve.

14. A shuttle valve as recited in claim 13, wherein:
an opposite end of the substantially cylindrical wall of the body of the shuttle valve is at least partially open and communicates with the atmosphere external of the shuttle valve.

15. A shuttle valve as recited in claim 14, wherein the shuttle valve further comprises:
a filter disposed at the opposite end of the substantially cylindrical wall of the body and secured to the body.

16. A shuttle valve as recited in claim 13, wherein:
the inlet and outlet ports are spaced apart from one another and extend away from the substantially cylindrical wall.

17. A shuttle valve as recited in claim 12, wherein:
the shuttle valve further comprises first and second annular seals, the first annular seal being disposed about the periphery of the disk and in slidable, sealing engagement with the inner surface of the body of the shuttle valve, the second annular seal being disposed about the periphery of the annular member and in slidable, sealing engagement with the inner surface of the body of the shuttle valve;
the second annular seal is effective for closing the outlet port when the shuttle is in the first position and for closing the inlet port when the shuttle is in the second position whereby the inlet and outlet ports are fluidicly uncoupled.

18. A shuttle valve as recited in claim 12, wherein:
the shuttle further includes a plurality of circumferentially spaced, radially extending spokes integral with and extending between the stem and the annular member;
the circumferentially spaced spokes permit the common port and the disk to be fluidicly coupled.

19. A shuttle valve as recited in claim 12, further comprising:
at least one stop protruding inwardly from the inner surface of the substantially cylindrical wall, the stops being effective for limiting the translation of the shuttle in at least one direction within the chamber.

20. A shuttle valve as recited in claim 1, wherein:
the outlet port is positioned longitudinally intermediate the common port and the inlet port.

21. A shuttle valve as recited in claim 1, wherein:
the body of the shuttle valve comprises first, second and third substantially cylindrical portions, the first portion being open at both ends, the second portion being disposed at least partially within one of the open ends of the first portion and the third portion being at least partially disposed within the other open end of the first portion.

22. A shuttle valve as recited in claim 21, wherein:
the second portion of the body of the shuttle valve is integrally formed with the common port.

23. A shuttle valve as recited in claim 21, wherein:
the third portion of the body of the shuttle valve is open at one end for receiving the shuttle therethrough, the other end of the third portion comprising a transverse wall having a vent passage formed therethrough, the vent passage fluidicly coupling the interior chamber and the atmosphere exterior of the valve.

24. A shuttle valve as recited in claim 21, wherein:
the first portion of the body of the shuttle valve includes a generally centrally disposed shoulder protruding inwardly from a remaining portion of the first portion of the body into the interior chamber, the second and third portions each having an open end in abutting relationship with the shoulder.

25. A shuttle valve as recited in claim 24, wherein:
the body of the shuttle valve has a substantially cylindrical inner surface having a first diameter;
the inner surface of the body of the shuttle valve comprises an inner surface of the second portion of the body, an inner surface of the shoulder and an inner surface of the third portion of the body.

26. A shuttle valve as recited in claim 21, wherein:
the body of the shuttle valve has a substantially cylindrical inner surface having a first diameter;
the shuttle includes a body portion having a substantially cylindrical outer surface having a second diameter that is substantially the same as the first diameter;
the outer surface of the body portion of the shuttle has a plurality of longitudinally spaced annular recesses formed therein;
the shuttle valve further includes a plurality of annular, elastomeric seals, each of the seals being disposed within one of the recesses and in slidable, sealing engagement with the inner surface of the body of the shuttle valve.

27. A shuttle valve as recited in claim 26, wherein the shuttle further includes:
a longitudinally extending passage and a plurality of radially extending passages disposed within the body portion, the longitudinally extending passage being fluidicly coupled with the common port at one end thereof and fluidicly coupled with the radially extending passages proximate an opposite end thereof, each of the radially extending passages having a distal end opening onto the outer surface of the body portion.

28. A shuttle valve comprising:
a body defining an interior chamber;
an inlet port, an outlet port and a common port, each of the ports being coupled to the body;
a shuttle translatably disposed within the chamber between a first position wherein the inlet port and the common port are fluidicly coupled and the common port and the outlet port are fluidicly uncoupled and a second position wherein the outlet port and the common port are fluidicly coupled and the common port and the inlet port are fluidicly uncoupled;
a first check valve coupled to the inlet port in a manner to permit fluid flow through the inlet port into the chamber and to prevent fluid from discharging from the chamber through the inlet port;
a second check valve coupled to the outlet port in a manner to permit fluid to discharge from the chamber through the outlet port and to prevent fluid from flowing through the outlet port into the chamber; and
a vent passage having a first end communicating with the interior chamber and a second end opening onto an outer surface of the body, wherein a portion of the interior chamber is vented to atmospheric pressure via the vent passage.

29. A shuttle valve as recited in claim 28, wherein:
the first end of the vent passage communicates with the interior chamber at a location proximate the outlet port.

30. A shuttle valve comprising:
a body defining an interior chamber;
an inlet port, an outlet port and a common port, each of the ports being coupled to the body;
a shuttle translatably disposed within the chamber between a first position wherein the inlet port and the common port are fluidicly coupled and the common port and the outlet port are fluidicly uncoupled and a second position wherein the outlet port and the common port are fluidicly coupled and the common port and the inlet port are fluidicly uncoupled;
a first check valve coupled to the inlet port in a manner to permit fluid flow through the inlet port into the chamber and to prevent fluid from discharging from the chamber through the inlet port;
a second check valve coupled to the outlet port in a manner to permit fluid to discharge from the chamber through the outlet port and to prevent fluid from flowing through the outlet port into the chamber;
wherein the shuttle comprises:
a substantially cylindrical body portion having an external surface with a first diameter;
a longitudinally extending passage having a proximal end fluidicly coupled with the common port and a distal end terminating within the body portion of the shuttle; and
a plurality of radially extending passages, each fluidicly coupled with the distal end of the longitudinally extending passage at one end thereof and opening onto the external surface at the other end thereof.

31. A shuttle valve as recited in claim 30, wherein the shuttle further comprises:
a pair of longitudinally spaced annular seals extending away from the external surface of the body portion of the shuttle, the plurality of radially extending passages opening onto the external surface intermediate of the annular seals; wherein
the body of the shuttle valve has a substantially cylindrical wall with an inner surface having a second diameter greater than the first diameter, the annular seals being disposed in slidable, sealing engagement with the inner surface to create an annular cavity;
the annular cavity is fluidicly coupled with the common port, the annular cavity being translatable with the shuttle within the interior chamber of said body of the shuttle valve such that the annular cavity is fluidicly coupled with the common port and the inlet port when the valve is in the first position and is fluidicly coupled with the common port and the outlet port when the valve is in the second position.

32. A shuttle valve as recited in claim 31, wherein:
the shuttle valve further includes an outlet passage having a first end fluidicly coupled with the annular cavity when the valve is in the second position and a second end fluidicly coupled with the outlet port.

33. A shuttle valve as recited in claim 32, wherein:
the outlet passage includes an opening that extends through the substantially cylindrical wall of the body, a longitudinally extending portion that extends along the outer surface of the body portion and an inwardly extending portion that extends within the interior chamber of the shuttle valve, the second portion being fluidicly coupled with the first portion and the outlet port.

34. A shuttle valve comprising:
a body defining an interior chamber;
an inlet port, an outlet port and a common port, each of the ports being coupled to the body;
a shuttle translatably disposed within the chamber between a first position wherein the inlet port and the common port are fluidicly coupled and the common port and the outlet port are fluidicly uncoupled and a second position wherein the outlet port and the common port are fluidicly coupled and the common port and the inlet port are fluidicly uncoupled;

a first check valve coupled to the inlet port in a manner to permit fluid flow through the inlet port into the chamber and to prevent fluid from discharging from the chamber through the inlet port;

a second check valve coupled to the outlet port in a manner to permit fluid to discharge from the chamber through the outlet port and to prevent fluid from flowing through the outlet port into the chamber;

wherein:

the body of the shuttle valve has a substantially cylindrical inner surface having a first diameter;

the shuttle includes a body portion having a substantially cylindrical outer surface with a second diameter less than the first diameter;

the shuttle further includes a plurality of longitudinally spaced seals extending outwardly from the body portion of the shuttle and disposed in slidable, sealing engagement with the inner surface of the body of the shuttle valve, the seals defining first, second and third annular cavities within the chamber between the outer surface of the body portion of the shuttle and the inner surface of the body of the shuttle valve, the first annular cavity being disposed proximate one end of the body portion and the third annular cavity being disposed proximate the other end of the body portion, the second annular cavity being disposed intermediate the first and third annular cavities;

the second cavity is in fluid communication with the common port and one of the inlet and outlet ports with the other of the inlet and outlet ports being in fluid communication with one of the first and third cavities, whereby fluid flow is permitted between the common port and one of the inlet and outlet ports and fluid flow between the inlet and outlet ports is prevented.

35. A system for dispensing a medical fluid intravenously to a patient comprising:

a shuttle valve having a body defining an interior chamber, and having an inlet port, an outlet port and a common port;

an unbiased shuttle translatably disposed within the chamber between a first position wherein the inlet port and the common port are fluidicly coupled and the common port and outlet port are fluidicly uncoupled and a second position wherein the outlet port and the common port are fluidicly coupled and the common port and the inlet port are fluidicly uncoupled;

a first check valve coupled to the inlet port in a manner to permit fluid flow through the inlet port into the chamber and to prevent fluid from discharging from the chamber through the inlet port;

a second check valve coupled to the outlet port in a manner to permit fluid to discharge from the chamber through the outlet port and to prevent fluid from flowing through the outlet port into the chamber;

a first section of tubing coupled at one end thereof to the inlet port and configured at an opposite end thereof for coupling to a reservoir of the fluid to be dispensed to the patient; and a second section of tubing coupled at one end thereof to the outlet port and configured at the other end thereof to be coupled to a patient.

36. A method for automatically selecting the ports of a valve in a fluid dispensing system to be fluidicly coupled, the valve including a body defining an interior chamber and further including an inlet port, an outlet port and a common port, each port being coupled to the body, the method comprising the steps of:

coupling a first check valve to the inlet port in a manner to permit fluid flow through the inlet into the chamber and to prevent fluid from discharging from the chamber through the inlet port;

coupling a second check valve to the outlet port in a manner to permit fluid to discharge from the chamber through the outlet port and to prevent fluid from flowing through the outlet port into the chamber;

disposing a shuttle within the interior chamber so that the shuttle is translatable between a first position wherein the inlet port and common port are fluidicly coupled and the common port and outlet port are fluidicly uncoupled and a second position wherein the outlet port and the common port are fluidicly coupled and the common port and the inlet port are fluidicly uncoupled;

venting at least a portion of the interior chamber to atmosphere.

37. A method as recited in claim 36, further comprising the step of:

configuring the valve so the inlet port and the outlet port are always fluidicly uncoupled, regardless of the position of the shuttle.

38. A method as recited in claim 37, wherein the step of configuring comprises:

providing at least two longitudinally spaced seals, the seals being disposed about a periphery of the shuttle and in slidable, sealing engagement with an inner surface of the body of the valve.

39. A method for dispensing a medical fluid intravenously to a patient comprising:

obtaining a shuttle valve having a body defining an interior chamber and further including inlet, outlet and common ports, each coupled to the body, a first check valve coupled to the inlet port in a manner to permit fluid flow through the inlet port into the interior chamber and to prevent fluid from discharging from the interior chamber through the inlet port, and a shuttle translatably disposed within the chamber;

inducing a negative pressure at the common port causing the shuttle to be disposed in a first position wherein the inlet port and the common port are fluidicly coupled and the common port and the outlet port are fluidicly uncoupled; and inducing a positive pressure at the common port causing the shuttle to be disposed in a second position wherein the outlet port and the common port are fluidicly coupled and the common port and the inlet port are fluidicly uncoupled;

wherein the shuttle changes position from the first position to the second position and from the second position to the first position solely in response to pressure of fluid intended to be communicated through the common port.

40. A method as recited in claim 39, wherein:

the step of inducing a negative pressure at the common port is accomplished by retracting a plunger of a syringe fluidicly coupled with the common port, whereby the syringe is at least partially filled with the medical fluid flowing through the inlet port;

the step of inducing a positive pressure at the common port is accomplished by advancing the plunger of the syringe, whereby the medical fluid is expelled out of the syringe and through the outlet port to the patient.

* * * * *

UNITED STATES PATENT AND TRADEMARK OFFICE
CERTIFICATE OF CORRECTION

| | | |
|---|---|---|
| PATENT NO. | : 7,637,279 B2 | Page 1 of 1 |
| APPLICATION NO. | : 11/275646 | |
| DATED | : December 29, 2009 | |
| INVENTOR(S) | : Joseph M. Amley et al. | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by 306 days.

Delete the phrase "by 306 days" and insert -- by 649 days --

Signed and Sealed this

Thirty-first Day of August, 2010

David J. Kappos
*Director of the United States Patent and Trademark Office*